United States Patent [19]
Breipohl et al.

[11] Patent Number: 5,597,803
[45] Date of Patent: Jan. 28, 1997

[54] BRADYKININ PEPTIDES WITH MODIFICATIONS AT THE N TERMINUS

[75] Inventors: Gerhard Breipohl, Frankfurt am Main; Stephan Henke, Hofheim am Taunus; Jochen Knolle, Kriftel/Ts.; Bernward Schölkens, Kelkheim; Hans-Georg Alpermann, Königstein/Taunus; Hermann Gerhards, Hofheim am Taunus; Klaus Wirth, Kriftel/Taunus, all of Germany

[73] Assignee: Hoechst Aktiengesellschaft, Frankfurt am Main, Germany

[21] Appl. No.: 373,464

[22] Filed: Jan. 17, 1995

Related U.S. Application Data

[63] Continuation of Ser. No. 41,176, Apr. 1, 1993, abandoned.

[30] Foreign Application Priority Data

Apr. 4, 1992 [DE] Germany .................. 42 11 406.3

[51] Int. Cl.$^6$ .................. A61K 38/00; A61K 38/04; C07K 5/00; C07K 7/00
[52] U.S. Cl. .................. 514/15; 514/16; 514/17; 530/314; 530/328; 530/329
[58] Field of Search .................. 514/15, 16, 17; 530/314, 327, 328, 329

[56] References Cited

U.S. PATENT DOCUMENTS

| | | |
|---|---|---|
| 4,344,949 | 8/1982 | Hoefle et al. . |
| 4,350,704 | 9/1982 | Hoefle et al. . |
| 4,374,847 | 2/1983 | Gruenfeld . |

FOREIGN PATENT DOCUMENTS

| | | |
|---|---|---|
| 03700453A2 | 11/1989 | European Pat. Off. . |
| 0370453A3 | 5/1990 | European Pat. Off. . |
| 0413277A1 | 8/1990 | European Pat. Off. . |
| 0455133A2 | 4/1991 | European Pat. Off. . |
| 0455133A3 | 11/1991 | European Pat. Off. . |
| 0472220A1 | 2/1992 | European Pat. Off. . |
| 906381 | 2/1991 | U.S.S.R. . |
| WO86/07263 | 12/1986 | WIPO . |
| WO89/01781 | 3/1989 | WIPO . |
| WO91/09055 | 6/1991 | WIPO . |

OTHER PUBLICATIONS

Stewart, John M., et al., "Bradykinin Chemistry: Agonists and Antagonists" Proceedings of the International Conference Kinin 81, pp. 585–589, published by Plenum Press, New York, (1983).

Primary Examiner—Avis M. Davenport
Attorney, Agent, or Firm—Finnegan, Henderson, Farabow, Garrett & Dunner, L.L.P.

[57] ABSTRACT

Peptides of the formula I $$Z\text{-}P\text{-}A\text{-}B\text{-}C\text{-}E\text{-}F\text{-}K\text{-}(D)Q\text{-}G\text{-}M\text{-}F'\text{-}I \quad (I)$$

and the physiologically tolerated salts thereof, are described.

They have an excellent bradykinin-antagonistic action.

They are obtained by reacting reacting a fragment with a C-terminal free carboxyl group or its activated derivative with a corresponding fragment with an N-terminal free amino group or assembling the peptide stepwise, where appropriate eliminating in the compound obtained in this way one or more protective groups introduced temporarily to protect other functionalities, and where appropriate converting the compounds of the formula I obtained in this way into the physiologically tolerated salt thereof.

3 Claims, No Drawings

BRADYKININ PEPTIDES WITH MODIFICATIONS AT THE N TERMINUS

This application is a continuation of application Ser. No. 08/041,176 filed Apr. 1, 1993, now abandoned.

The invention relates to novel peptides with a bradykinin-antagonistic action and to a process for the preparation thereof.

Bradykinin-antagonistic peptides are described, inter alia, in WO 86/07263 and European Patent Applications No.370 453, No. 413 277, No. 455 133 and No. 472 220.

The present invention describes novel peptides with a bradykinin-antagonistic action of the formula I $$Z\text{-}P\text{-}A\text{-}B\text{-}C\text{-}E\text{-}F\text{-}K\text{-}(D)Q\text{-}G\text{-}M\text{-}F'\text{-}1 \qquad (I),$$

in which
Z is $a_1$)
  $(C_1-C_8)$-alkyl,
  $(C_1-C_8)$-alkanoyl,
  $(C_1-C_8)$-alkoxycarbonyl
  $(C_3-C_8)$-cycloalkyl,
  $(C_4-C_9)$-cycloalkanoyl, or
  $(C_1-C_8)$-alkylsulfonyl,
    in which, in each case, 1, 2 or 3 hydrogen atoms are optionally replaced by 1, 2 or 3 identical or different radicals from the series comprising
    carboxyl,
    $NHR^1$, $((C_1-C_4)\text{-alkyl})NR^1$ or $((C_6-C_{10})\text{-aryl-}(C_1-C_4)\text{-alkyl})NR^1$, where $R^1$ is hydrogen or a urethane protective group,
    $(C_1-C_4)$-alkyl,
    $(C_1-C_8)$-alkylamino,
    $(C_1-C_{10})$-aryl-$(C_1-C_4)$-alkylamino,
    hydroxyl,
    $(C_1-C_4)$-alkoxy,
    halogen,
    di-$(C_1-C_8)$-alkylamino,
    di-$[(C_6-C_{10})$-aryl-$(C_1-C_4)]$-alkylamino,
    carbamoyl,
    phthalimido,
    1,8-naphthalimido,
    sulfamoyl,
    $(C_1-C_4)$-alkoxycarbonyl,
    $(C_6-C_{14})$-aryl and
    $(C_6-C_{14})$-aryl-$(C_1-C_5)$-alkyl,
  or in which, in each case, 1 hydrogen atom is optionally replaced by a radical from the series comprising
    $(C_3-C_8)$-cycloalkyl,
    $(C_1-C_6)$-alkylsulfonyl,
    $(C_1-C_6)$-alkylsulfinyl,
    $(C_6-C_{14})$-aryl-$(C_1-C_4)$-alkylsulfonyl,
    $(C_6-C_{14})$-aryl-$(C_1-C_4)$-alkylsulfinyl,
    $(C_6-C_{14})$-aryl,
    $(C_6-C_{14})$-aryloxy,
    $(C_3-C_{13})$-heteroaryl and
    $(C_3-C_{13})$-heteroaryloxy
  and 1 or 2 hydrogen atoms are replaced by 1 or 2 identical or different radicals from the series comprising
    carboxyl,
    amino,
    $(C_1-C_8)$-alkylamino,
    hydroxyl,
    $(C_1-C_4)$-alkoxy,
    halogen,
    di-$(C_1-C_8)$-alkylamino,
    carbamoyl,
    sulfamoyl,
    $(C_1-C_4)$-alkoxycarbonyl,
    $(C_1-C_4)$-aryl and
    $(C_6-C_{14})$-aryl-$(C_1-C_5)$-alkyl;
$a_2$)
  $(C_6-C_{14})$-aryl,
  $(C_7-C_{15})$-aroyl,
  $(C_6-C_{14})$-arylsulfonyl,
  $(C_3-C_{13})$-heteroaryl, or
  $(C_3-C_{13})$-heteroaroyl;
$a_3$) carbamoyl which can optionally be substituted on the nitrogen by
  $(C_1-C_8)$-alkyl,
  $(C_6-C_{14})$-aryl or
  $(C_6-C_{14})$-aryl-$(C_1-C_5)$-alkyl;
where, in the radicals defined under $a_1$), $a_2$) and $a_3$), in each case aryl, heteroaryl, aroyl, arylsulfonyl and heteroaroyl is optionally substituted by 1, 2, 3 or 4 identical or different radicals from the series comprising
  carboxyl,
  amino,
  nitro,
  $(C_1-C_8)$-alkylamino,
  hydroxyl,
  $(C_1-C_6)$-alkyl,
  $(C_1-C_6)$-alkoxy,
  $(C_6-C_{14})$-aryl,
  $(C_7-C_{15})$-aroyl,
  halogen,
  cyano,
  di-$(C_1-C_8)$-alkylamino,
  carbamoyl,
  sulfamoyl and,
  $(C_1-C_6)$-alkoxycarbonyl;
P is a direct linkage, or is a radical of the formula II $$-NR^2-(U)-CO \qquad (II)$$

in which
$R^2$ is hydrogen, methyl or a urethane protective group,
U is a $(C_3-C_8)$-cycloalkylidene, $(C_8-C_{14})$-arylidene, $(C_3-C_{13})$-heteroarylidene,$(C_6-C_{14})$-aryl-$(C_1-C_5)$-alkylidene, each of which can optionally be substituted, or is $(CHR^3)_n$,
where n is 1–8, preferably 1–6,
$R^3$ is, independently of one another, hydrogen,
  $(C_1-C_6)$-alkyl,
  $(C_3-C_8)$-cycloalkyl,
  $(C_6-C_{14})$-aryl,
  $(C_3-C_{13})$-heteroaryl which is in each case optionally monosubstituted by
    amino,
    substituted amino,
    amidino
    substituted amidino
    hydroxyl,
    carboxyl,
    carbamoyl,
    guanidino,
    substituted guanidino,
    ureido,
    substituted ureido,
    mercapto, methylmercapto,
phenyl,
4-chlorophenyl,
4-fluorophenyl,
4-nitrophenyl,
4-methoxyphenyl,
4-hydroxyphenyl,
phthalimido,
1,8-naphthalimido,
4-imidazolyl,
3-indolyl,
2-thienyl,
3-thienyl,
2-pyridyl,
3-pyridyl or
cyclohexyl, where substituted amino is preferably —N(A')—Z, substituted amidino is preferably —(NH═)C—NH—Z, substituted guanidino is preferably —N(A')—C(═N(A'))—NH—Z and substituted ureido is preferably —CO—N(A')—Z, in which A' is, independently of one another, hydrogen or Z, where Z is as defined under $a_1$) or $a_2$); or in which $R^2$ and $R^3$ together with atoms carrying them form a mono-, bi- or tricyclic ring system with 2 to 15 carbon atoms;

A is defined as P;
B is a basic amino acid in the L or D configuration, which can be substituted in the side chain;
C is a compound of the formula IIIa or IIIb

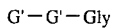  (IIIa)

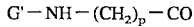  (IIIb)

in which
p is 2 to 8 and
G' is, independently of one another, a radical of the formula IV

  (IV)

in which
$R^4$ and $R^5$ together with the atoms carrying them form a heterocyclic mono-, bi- or tricyclic ring system with 2 to 15 carbon atoms;
E is the residue of a neutral, acidic or basic, aliphatic or alicyclic-aliphatic amino acid;
F is, independently of one another, the residue of a neutral, acidic or basic, aliphatic or aromatic amino acid which can be substituted in the side chain, or is a direct linkage;
(D)Q is D-Tic, D-Phe, D-Dic, D-Thi or D-Nal, each of which can optionally be substituted by halogen, methyl or methoxy, or is a radical of the formula

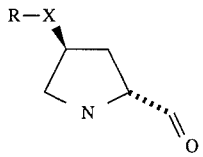  (V)

in which
X is oxygen, sulfur or a direct linkage;
R is hydrogen, $(C_1-C_8)$-alkyl, $(C_3-C_8)$-cycloalkyl, $(C_6-C_{14})$-aryl, $(C_6-C_{14})$-aryl-$(C_1-C_4)$-alkyl, where cycloalkyl can optionally be substituted by halogen, methyl or methoxy;

G is defined as G' above or is a direct linkage;
F' is defined as F, is a radical —NH—$(CH_2)_q$- with q=2 to 8, or can be a direct linkage if G is not a direct linkage;
I is —OH, —$NH_2$ or $NHC_2H_5$;
K is the radical —NH—$(CH_2)_x$—CO— with x=1–4, or is a direct linkage, and
M is defined as F,
and the physiologically tolerated salts thereof.

Unless otherwise indicated, the abbreviation of an amino acid residue without a stereo descriptor stands for the residue in the L form (cf. Schröder, Lübke, Peptides, Volume 1, New York 1965, pages XXII–XXIII; Houben-Weyl, Methoden der Organischen Chemie (Methods of organic chemistry) Volume XV/1 and 2, Stuttgart 1974), such as, for example, Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, hArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val etc.

Particularly suitable as radical of a heterocyclic ring system of the formula IV are radicals of heterocycles from the following group:

Pyrrolidine-2-carboxylic acid; piperidine-2-carboxylic acid; 1,2,3,4-tetrahydroisoquinoline-3-carboxylic acid; decahydroisoquinoline-3-carboxylicacid;octahydroindole-2-carboxylic acid; decahydroquinoline-2-carboxylic acid; octahydrocyclopenta[b]pyrrole-2-carboxylic acid;
2-azabicyclo[2.2.2]octane-3-carboxylic acid;
2-azabicyclo[2.2.1]heptane-3-carboxylic acid;
2-azabicyclo[3.1.0]hexane-3-carboxylic acid;
2-azaspiro[4.4]nonane-3-carboxylic acid;
2-azaspiro[4.5]decane-3-carboxylic acid;
spiro[(bicyclo[2.2.1]heptane)-2,3-pyrrolidine-5-carboxylic acid];
spiro[(bicyclo[2.2.2]octane)-2,3-pyrrolidine-5-carboxylic acid];
2-azatricyclo[4.3.0.1$^{6,9}$]decane-3-carboxylic acid;
decahydrocyclohepta[b]pyrrole-2-carboxylic acid;
decahydrocycloocta[b]pyrrole-2-carboxylic acid;
octahydrocyclopenta[c]pyrrole-2-carboxylic acid;
octahydroisoindole-1-carboxylic acid;
2,3,3a,4,6a-hexahydrocyclopenta[b]pyrrole-2-carboxylic acid;
2,3,3a,4,5,7a-hexahydroindole-2-carboxylic acid;
tetrahydrothiazole-4-carboxylic acid;
isoxazolidine-3-carboxylic acid; pyrazolidine-3-carboxylic acid; hydroxypyrrolidine-2-carboxylic acid; all of which can optionally be substituted:

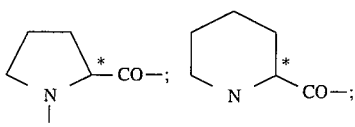

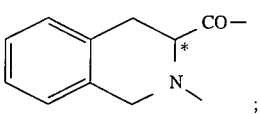

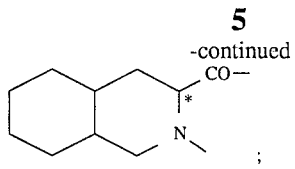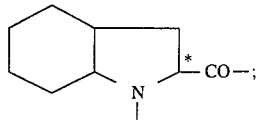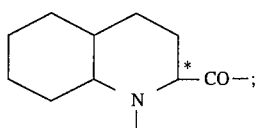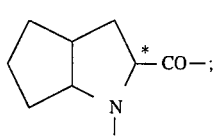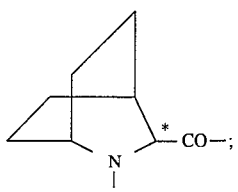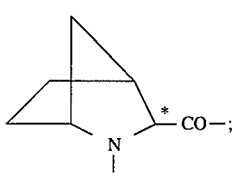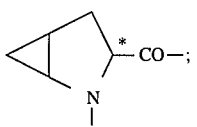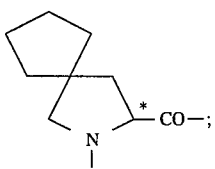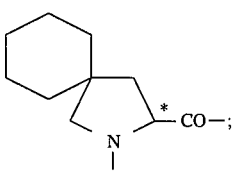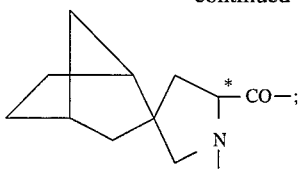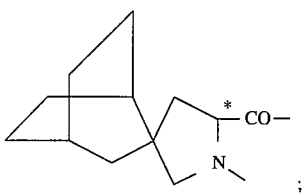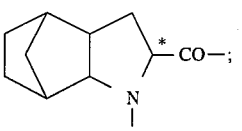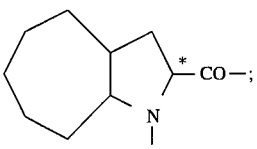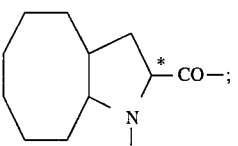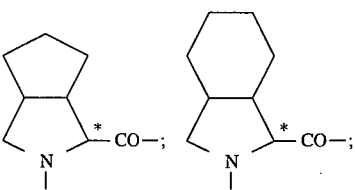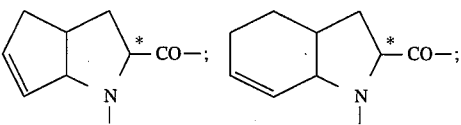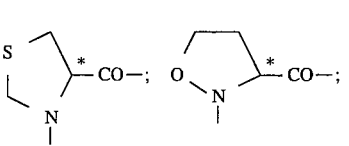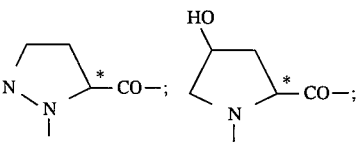

The heterocycles from which the abovementioned radicals are derived are disclosed, for example, in U.S. Pat. Nos. 4,344,949, 4,374,847, 4,350,704, EP-A 29 488, EP-A 31 741, EP-A 46 953, EP-A 49 605, EP-A 49 658, EP-A 50 800, EP-A 51 020, EP-A 52 870, EP-A 79 022, EP-A 84 164, EP-A 89 637, EP-A 90 341, EP-A 90 362, EP-A 105 102, EP-A 109 020, EP-A 111 873, EP-A 271 865 and EP-A 344 682.

Unless otherwise indicated in the individual case, alkyl can be straight-chain or branched. A corresponding statement applies to radicals derived therefrom, such as, for example, alkoxy, aralkyl or alkanoyl.

$(C_6-C_{12})$-aryl is preferably phenyl, naphthyl, biphenylyl, fluorenyl or phenanthrenyl. Radicals derived therefrom, such as, for example, aryloxy, aralkyl or aroyl are to be formulated correspondingly.

Halogen is fluorine, chlorine, bromine or iodine, preferably chlorine or fluorine.

Urethane protective groups are described, for example, in A. Hubbuch, Kontakte Merck 3/79, pages 14–23, and Fmoc and Cbz are preferred.

Suitable salts are, in particular, alkali metal or alkaline earth metal salts, salts with physiologically tolerated amines and salts with inorganic or organic acids such as, for example, HCl, HBr, $H_2SO_4$, $H_3PO_4$, maleic acid, fumaric acid, citric acid, tartaric acid, acetic acid.

Preferred peptides of the formula I are those in which

B is Arg, Lys, Orn, 2,4-diaminobutyryl or a L-homoarginine residue, it being possible in each case for the amino or the guanidino group of the side chain to be substituted by Z as described under $a_1$) or $a_2$);

E is the residue of an aliphatic or alicyclic aliphatic amino acid in the L or D configuration, which contains 1 to 14 carbon atoms in the side chain, such as thienylalanine, phenylalanine, alanine, serine, threonine, O-$(C_1-C_6)$-alkyl or O-$(C_6-C_{10})$-aryl protected serine or threonine, valine, norvaline, leucine, isoleucine, norleucine, neopentylglycine, tert.-butylglycine or $(C_3-C_7)$-cycloalkyl-$(C_1-C_3)$-alkylglycine;

F' is the residue of a basic amino acid in the L or D configuration, such as Arg, hArg, Orn or Lys, it being possible for the guanidino group or amino group in the side chain to be substituted by Z as described under $a_1$) or $a_2$), or a radical —NH$(CH_2)_q$— with q=2 to 8;

K is the radical —NH—$(CH_2)_x$—CO— with x=2–4 or is a direct linkage.

Particularly preferred peptides of the formula I are those in which

B is Arg, hArg, Orn or Lys, where the guanidino group or the amino group of the side chain is unsusbtituted or can be substituted by $(C_1-C_4)$-alkyl, trifluoromethyl-$(C_1-C_4)$-alkyl, $(C_1-C_8)$-alkanoyl, $(C_7-C_{13})$-aroyl, $(C_3-C_{13})$-heteroaroyl, $(C_1-C_8)$-alkylsulfonyl or $(C_6-C_{14})$-arylsulfonyl, it being possible for the aryl, heteroaryl, aroyl, arylsulfonyl and heteroaroyl radicals to be substituted as described under a2) with optionally 1, 2, 3 or 4 identical or different radicals;

E is thienylalanine, phenylalanine, leucine, isoleucine, norleucine or cyclohexylalanine;

K is a direct linkage;

(D)Q is D-Tic or D-Phe, each of which can be optionally substituted by halogen, methyl or methoxy, or is a radical of the formula V in which X is oxygen, sulfur or a direct linkage, and R is $(C_1-C_6)$-alkyl, $(C_3-C_6)$-cycloalkyl, phenyl or benzyl, and M is a direct linkage.

Very particularly preferred peptides of the formula I are those in which

Z is $a_1$)
$(C_1-C_8)$-alkyl,
$(C_1-C_8)$-alkanoyl,
$(C_1-C_8)$-alkoxycarbonyl
$(C_3-C_8)$-cycloalkyl,
$(C_4-C_9)$-cycloalkanoyl, or
$(C_1-C_8)$-alkylsulfonyl,
in which, in each case, 1, 2 or 3 hydrogen atoms are optionally replaced by 1, 2 or 3 identical or different radicals from the series comprising
NHR$^1$, (($C_1-C_4$)-alkyl)NR$^1$ or (($C_6-C_{10}$)-aryl-($C_1-C_4$)-alkyl-NR$^1$, where R$^1$ is hydrogen or a urethane protective group,
$(C_1-C_4)$-alkyl,
$(C_1C_8)$-alkylamino,
$(C_6-C_{10})$-aryl-$(C_1-C_4)$-alkylamino,
$(C_1-C_4)$-alkoxy,
halogen,
di-$(C_1-C_8)$-alkylamino,
di-[$(C_6-C_{10})$-aryl-$(C_1-C_4)$]-alkylamino,
phthalimido,
1,8-naphthalimido,
$(C_6-C_{14})$-aryl and
$(C_6-C_{14})$-aryl-$(C_1-C_5)$-alkyl,
or in which, in each case, 1 hydrogen atom is optionally replaced by a radical from the series comprising
$(C_3-C_8)$-cycloalkyl,
$(C_1-C_6)$-alkylsulfonyl,
$(C_1-C_6)$-alkylsulfinyl,
$(C_6-C_{14})$-aryl-$(C_1-C_4)$-alkylsulfonyl,
$(C_6-C_{14})$-aryl-$(C_1-C_4)$-alkylsulfinyl,
$(C_6-C_{14})$-aryl,
$(C_6-C_{14})$-aryloxy and
$(C_3-C_{13})$-heteroaryl
and 1 or 2 hydrogen atoms are replaced by 1 or 2 identical or different radicals from the series comprising
amino,
$(C_1-C_8)$-alkylamino,
di-$(C_1-C_8)$-alkylamino,
carbamoyl and
sulfamoyl;

$a_2$)
$(C_6-C_{14})$-aryl,
$(C_7-C_{15})$-aroyl,
$(C_6-C_{14})$-arylsulfonyl,
$(C_3-C_{13})$-heteroaryl, or
$(C_3-C_{13})$-heteroaroyl;

$a_3$) carbamoyl which can optionally be substituted on the nitrogen by
$(C_1-C_8)$-alkyl,
$(C_6-C_{14})$-aryl or
$(C_6-C_{14})$-aryl-$(C_1-C_5)$-alkyl;

where, in the radicals defined under $a_1$), $a_2$) and $a_3$), in each case aryl, heteroaryl, aroyl, arylsulfonyl and heteroaroyl is optionally substituted by 1, 2, 3 or 4 identical or different radicals from the series comprising
amino,
nitro,
$(C_1-C_8)$-alkylamino,
$(C_1-C_6)$-alkyl,
$(C_1-C_6)$-alkoxy,
$(C_6-C_{14})$-aryl,
$(C_7-C_{15})$-aroyl,
halogen,
di-$(C_1-C_8)$-alkylamino and carbamoyl;

P is a direct linkage, or is a radical of the formula II in which

R² is hydrogen, methyl or a urethane protective group,

U is a $(C_3-C_8)$-cycloalkylidene, $(C_6-C_{14})$-arylidene, $(C_3-C_{13})$-heteroarylidene, $(C_6-C_{14})$-aryl-$(C_1-C_5)$-alkylidene, each of which can optionally be substituted, or is $(CHR^3)_n$, where n is 1–6, R³ is, independently of one another, hydrogen,
$(C_1-C_6)$-alkyl,
$(C_3-C_6)$-cycloalkyl,
$(C_6-C_{14})$-aryl, which is in each case optionally monosubstituted by
amino,
substituted amino,
amidino
substituted amidino
carbamoyl,
guanidino,
substituted guanidino,
ureido,
substituted ureido,
phenyl,
4-fluorophenyl,
4-methoxyphenyl,
phthalimido,
1,8-naphthalimido,
3-indolyl,
2-thienyl,
3-thienyl or
cyclohexyl, where substituted amino is preferably —N(A')—Z, substituted amidino is preferably —(NH═)C—NH—Z, substituted guanidino is preferably —N(A')—C(═N(A'))—NH—Z and substituted ureido is preferably —CO—N(A')—Z, in which A' is, independently of one another, hydrogen or Z, where Z is as defined under $a_1$) or $a_2$); or in which R² and R³ together with atoms carrying them form a mono-, bi- or tricyclic ring system with 2 to 15 carbon atoms;

A is (D)- or (L)-Arg, (D)- or (L)-Lys, (D)- or (L)-Orn or (D)- or (L)-hArg, it being possible for the guanidino group or the amino group of the side chain to be substituted by $(C_1-C_4)$-alkyl or trifluoromethyl-$(C_1-C_4)$-alkyl, or is a bond;

B is Arg, Orn or Lys, it being possible for the guanidino group or the amino group of the side chain to be substituted by $(C_1-C_4)$-alkyl, trifluoromethyl-$(C_1-C_4)$-alkyl, $(C_1-C_8)$-alkanoyl, $(C_7-C_{13})$-aroyl, $(C_3-C_{13})$-heteroaroyl, $(C_1-C_8)$-alkylsulfonyl or $(C_6-C_{14})$-arylsulfonyl, it being possible for the aryl, heteroaryl, aroyl, arylsulfonyl and heteroaroyl radicals optionally to be substituted by 1,2, 3 or 4 identical or different radicals from the series comprising methyl, methoxy and halogen;

C is Pro-Pro-Gly, Hyp-Pro-Gly or Pro-Hyp-Gly;

E is Thia, Phe, Leu or Cha;

F is Ser, Cys, Leu, Val, Nle, Ile or Thr;

K is a direct linkage;

Q is Tic, Phe or a radical of the formula V in which X is oxygen and R is $(C_1-C_6)$-alkyl, or X is sulfur and R is phenyl or benzyl, or X is a direct linkage and R is cyclohexyl, phenyl or benzyl;

M is a direct linkage;

G is the radical of a heterocyclic ring system of the formula IV, where the radicals of the heterocycles pyrrolidine-2-carboxylic acid;piperidine-2-carboxylic acid, tetrahydroisoquinoline-3-carboxylic acid, cis- and trans-decahydroisoquinoline-3-carboxylic acid; cis-endo-, cis-exo-, trans-octahydroindole-2-carboxylic acid; cis-endo-, cis-exo-, trans-octahydrocyclopenta[b]pyrrole-2-carboxylic acid, pyrrolidine-2-carboxylic acid or 4-hydroxypyrrolidine-2-carboxylic acid are preferred;

F' is Arg which is optionally substituted in the guanidino group by Z as described under $a_1$) or $a_2$), or is a direct linkage and I is OH or $NH_2$.

The invention furthermore relates to a process for preparing peptides of the formula I, which comprises a) reacting a fragment with a C-terminal free carboxyl group or its activated derivative with a corresponding fragment with an N-terminal free amino group or b) assembling the peptide stepwise, where appropriate eliminating in the compound obtained as in (a) or (b) one or more protective groups introduced temporarily to protect other functionalities, and where appropriate converting the compounds of the formula I obtained in this way into the physiologically tolerated salt thereof.

The peptides of the present invention have been prepared by generally known methods of peptide chemistry, see, for example, Houben-Weyl, Methoden der organischen Chemie, Volume 15/2, preferably by solid-phase synthesis as described, for example, by B. Merrifield, J. Am. Chem. Soc. 85, 2149 (1963) or R. C. Sheppard, Int. J. Peptide Protein Res. 21, 118 (1983) or by equivalent known methods. Urethane protective groups such as, for example, the tert.-butyloxycarbonyl[Boc] or fluorenylmethyloxycarbonyl [Fmoc] protective group are used as temporary amino protective group. If necesary to prevent side reactions or for synthesising specific peptides, the functional groups in the side chain of the amino acids are additionally protected by suitable protective groups (see, for example, T. W. Greene, "Protective Groups in Organic Synthesis"), employing primarily Arg(Tos), Arg(Mts), Arg(Mtr), Arg(Pmc), Asp(OBzl), Asp(OBut), Cys(4-MeBzl), Cys(Acm), Cys(S-But), Glu(OBzl), Glu(OBut), His(Tos), His(Fmoc), His(Dnp), His(Trt), Lys(C1-Z), Lys(Boc), Met(O), Ser(Bzl), Set(But), Thr(Bzl), Thr(But), Trp(Mts), Trp(CHO), Trp(Boc), Tyr(Br-Z), Tyr(Bzl) or Tyr(But).

The solid-phase synthesis starts at the C-terminal end of the peptide by coupling a protected amino acid onto an appropriate resin. Starting materials of this type can be obtained by linking a protected amino acid via an ester or amide linkage to a polystyrene or polyacrylamide resin which is modified with a chloromethyl, hydroxymethyl, benzhydrylamino (BHA) or methylbenzhydrylamino (MBHA) group. The resins used as support material are commercially available. BHA- and MBHA-resins are usually employed when the synthesized peptide is to contain a free carbamoyl group at the C terminus. If the peptide is to contain a secondary amide group at the C-terminal end, a chloromethyl- or hydroxymethyl-resin is used, and the cleavage off is carried out with the appropriate amines. If, for example, it is wished to obtain the ethylamide, the peptide can be cleaved off the resin with ethylamine, in which case the elimination of the side-chain protective groups is subsequently carried out with other suitable reagents. If the tert.-butyl protective groups on the amino acid side chain are to be retained in the peptide, the synthesis is carried out with the Fmoc protective group for temporary blocking of the amino group which is used for chain extension in the amino acid, using the method described, for example, by R. C. Sheppard, J. Chem. Soc., Chem. Comm. 1982, 587, in which case the guanidino functionality of the arginine is protected by protonation with pyridinium perchlorate and the other amino acids functionalized in the side chain are protected by benzyl protective groups which can be eliminated by catalytic transfer hydrogenation (A. Felix et al., J. Org. Chem. 13, 4194 (1978)) or by sodium in liquid ammonia (W. Roberts, J. Am. Chem. Soc. 76, 6203 (1954)).

After elimination of the amino protective group on the amino acid coupled to the resin using a suitable reagent such as, for example, trifluoroacetic acid in methylene chloride in the case of the Boc protective group or a 20% strength solution of piperidine in dimethylformamide in the case of the Fmoc protective group, the following protected amino acids are coupled on successively in the required sequence. The peptide-resins with N-terminal protection which are produced as intermediates are deblocked by the previously described reagents before linkage to the subsequent amino acid derivative.

It is possible to use as coupling reagent all possible activation reagents used in peptide synthesis, see, for example, Houben-Weyl, Methoden der organischen Chemie, Volume 15/2, but especially carbodiimides such as, for example, N,N'-dicyclohexylcarbodiimide, N,N'-diisopropylcarbodiimide or N-ethyl-N'-(3-dimethylaminopropyl)carbodiimide or uronium compounds (for example TBTU, TOTU) as are described, for example, by R. Knorr et al. in Tetrahedron Letters, Vol. 30, No. 15, pp 1927–1930, 1989, or in European Patent Application No. 460 446. The coupling can moreover be carried out directly by addition of amino acid derivative with the activating reagent and, where appropriate, with an additive which suppresses racemization, such as, for example, 1-hydroxybenzotriazole (HOBt) (W. König, R. Geiger, Chem. Ber. 103,708 (1970)) or 3-hydroxy-4-oxo-3,4-dihydrobenzotriazine (HOObt) (W. König, R. Geiger, Chem. Ber. 103, 2054 (1970)) to the resin, or else the preactivation of the amino acid derivative as symmetric anhydride or HOBt or HOObt ester can take place separately, and the solution of the activated species in a suitable solvent can be added to the peptide-resin ready for coupling.

The coupling and activation of the amino acid derivatives with one of the abovementioned activating reagents can be carried out in dimethylformamide, N-methylpyrrolidone or methylene chloride or a mixture of the said solvents. The activated amino acid derivative is normally employed in a 1.5 to 4-fold excess. In cases where incomplete coupling occurs, the coupling reaction is repeated without previously carrying out the deblocking of the amino group on the peptide-resin which is necessary for coupling the next amino acid in sequence.

It is possible to check whether the coupling reaction has taken place successfully using the ninhydrin reaction as described, for example, by E. Kaiser et al., Anal. Biochem. 34, 595 (1970). The synthesis can also be carried out automatically, for example with a model 430A peptide synthesizer from Applied Biosystems, it being possible to use either the synthesis programs provided by the manufacturer of the apparatus or else those drawn up by the user himself. The latter are particularly employed when amino acid derivatives protected with the Fmoc group are used.

After the peptides have been synthesized in the manner described above, the peptide can be cleaved off the resin with reagents such as, for example, liquid hydrogen fluoride (preferred for the peptides prepared by the Boc method) or trifluoroacetic acid (preferred for the peptides synthesized by the Fmoc method). These reagents not only cleave the peptide off the resin but also eliminate the other side-chain protective groups on the amino acid derivatives. In this way, except when BHA- and MBHA-resins are used, the peptide is obtained in the form of the free acid. In the case of the BHA- and MBHA-resins, the peptide is obtained as amide on cleavage with hydrogen fluoride or trifluoromethanesulfonic acid. Other processes for preparing peptide amides are described in EP-A 287 882 and EP-A 322 348. In this case, the peptide amides are cleaved off the resin by treatment with the moderately strong acids customarily used in peptide synthesis (for example trifluoroacetic acid), adding as cation traps substances such as phenol, cresol, thiocresol, anisole, thioanisole, ethanedithiol, dimethyl sulfide, ethyl methyl sulfide or similar cation traps which are customary in solid-phase synthesis, singly or as a mixture of two or more of these aids. The trifluoroacetic acid can moreover be used diluted in suitable solvents such as, for example, methylene chloride. The cleavage can likewise be carried with a mixture of trifluoroacetic acid, trimethylsilyl halide (for example trimethylsilyl bromide) and a phenol (for example m-cresol). If the tert.-butyl or benzyl side-chain protective groups on the peptides are to be retained, the peptide which has been synthesized on a specially modified support resin is cleaved off with 1% trifluoroacetic acid in methylene chloride, as described, for example, by R. C. Sheppard, J. Chem. Soc., Chem. Comm. 1982, 587. If individual tert.-butyl or benzyl side-chain protective groups are to be retained, a suitable combination of the methods of synthesis and cleavage off is used.

The modified support resin described by Sheppard is likewise used for synthesizing peptides with a C-terminal carbamoyl group or an ω-amino- or ω-guanidinoalkyl group. After the synthesis, the peptide which is completely protected in the side chain is cleaved off the resin and subsequently reacted in classical solution synthesis with the appropriate amine or ω-aminoalkylamine or ω-guanidinoalkylamine, it being possible where appropriate for other functional groups which are present to be protected temporarily in a known manner.

Another process for preparing peptides with an ω-aminoalkyl group is described in EP-A 264 802.

The peptides of the present invention have preferably been synthesized using the solid-phase technique according to two general protective group tactics.

The synthesis was carried out with a model 430 A automatic peptide synthesizer from Applied Biosystems using Boc or Fmoc protective groups for temporary blocking of the amino group.

When the Boc protective group was used, the synthesis cycles preprogrammed by the manufacturer of the apparatus were employed for the synthesis.

The peptides with a free carboxyl group at the C-terminal end were synthesized on a 4-(hydroxymethyl)phenylacetamidomethylpolystyrene resin (R. B. Merrifield, J. Org. Chem. 43, 2845 (1978)) functionalized with the appropriate Boc-amino acid from Applied Biosystems. To prepare the peptide amides, an MBHA-resin from the same company was used. The activating reagents used were N,N'-dicyclohexylcarbodiimide or N,N'-diisopropylcarbodiimide. Activation took place as symmetric anhydride, as HOBt ester or HOObt ester in $CH_2Cl_2$, $CH_2Cl_2$/DMF-mixtures or NMP. 2–4 equivalents of activated amino acid derivative were employed for the coupling. In cases where the coupling took place incompletely, the reaction was repeated.

When the Fmoc protective group was used for temporary protection of the amino group, our own synthesis programs were input for the synthesis with the model 430A automatic peptide synthesizer from Applied Biosystems. Synthesis took place on a p-benzyloxybenzyl alcohol-resin (S. Wang, J. Am. Chem. Soc. 95, 1328 (1973)) from Bachem, which was esterified by a known method (E. Atherton et al., J. C. S. Chem. Comm. 1981, 336) with the appropriate amino acid. The amino acid derivatives were activated as HOBt or HOObt esters directly in the amino acid cartridges supplied by the manufacturer of the apparatus by adding a solution of diisopropylcarbodiimide in DMF to the mixture, which had previously been weighed in, of amino acid derivative and HOBt or HOObt. It is likewise possible to employ Fmoc-amino acid OObt esters prepared in bulk as described in EP-A 247 573. The Fmoc protective group was eliminated with a 20% strength solution of piperidine in DMF in the reaction vessel. The excess of reactive amino acid derivative used was 1.5 to 2.5 equivalents. If the coupling was incomplete, it was repeated as for the Boc method.

The peptides according to the invention have, singly or in combination, a bradykinin-antagonistic action which can be tested in various models (see Handbook of Exp. Pharmacol. Vol. 25, Springer Verlag, 1970, pages 53–55), for example on the isolated rat uterus, on the guinea pig ileum or on the isolated guinea pig pulmonary artery.

To test the peptides according to the invention on the isolated pulmonary artery, guinea pigs (Dunkin Hartley) weighing 400–450 g are sacrificed by a blow to the back of the neck. The thorax is opened and the pulmonary artery is carefully dissected out. The surrounding tissue is cautiously removed and the pulmonary artery is cut open in a spiral at an angle of 45°. The strip of vessel 2.5 cm long and 3–4 mm wide is fixed in an organ bath which has a capacity of 10 ml and is filled with Ringer solution.

| Composition of the solution in mmol/l | |
|---|---|
| NaCl | 154 |
| KCl | 5.6 |
| $CaCl_2$ | 1.9 |
| $NaHCO_3$ | 2.4 |
| glucose | 5.0 |

95% $O_2$ and 5% $CO_2$ is bubbled through the solution, which is heated to 37° C. The pH is 7.4 and the preload on the strip of vessel is 1.0 g.

The isometric contraction changes are detected using a lever attachment and an HF modem (position sensor) from Hugo Sachs and are recorded on a potentiometric recorder (BEC, Goerz Metrawatt SE 460).

The experiment is started after equilibration for 1 hour. After the strips of vessel have reached their maximum sensitivity to $2 \times 10^{-7}$ mol/l bradykinin—bradykinin leads to contraction of the strips of vessel—the peptides are left to act in doses of $5 \times 10^{-8}$–$1 \times 10^{-5}$ mol/l for 10 minutes each and, after renewed addition of bradykinin, the decrease in the effect of bradykinin is compared with the control.

To detect a partial agonistic effect, the peptides are used in doses of $1 \times 10^{-5}$–$1 \times 10^{-3}$ mol/l.

The $IC_{50}$ values of the peptides according to the invention, calculated from the dose-effect plots, are listed in Table 1.

TABLE 1

| Ex. No. | Sequence | $IC_{50}$ (pulmonary artery) |
|---|---|---|
| 1 | Fmoc—D—Arg—Arg—Pro—Hyp—Gly—Thia—Ser—D—Tic—Oic—Arg—OH | $9.9 \times 10^{-9}$ |
| 2 | Fmoc—Aoc—D—Arg—Arg—Pro—Hyp—Gly—Thia—Ser—D—Tic—Oic—Arg—OH | $8.5 \times 10^{-9}$ |
| 3 | Dibenzylacetyl-D—Arg—Arg—Pro—Hyp—Gly—Thia—Ser—D—Tic—Oic—Arg—OH | $1.7 \times 10^{-8}$ |
| 4 | Cyclohexylcarbonyl-D—Arg—Arg—Pro—Hyp—Gly—Thia—Ser—D—Tic—Oic—Arg—OH | $9.1 \times 10^{-9}$ |
| 5 | Fmoc-ε-aminocaproyl-D—Arg—Arg—Pro—Hyp—Gly—Thia—Ser—D—Tic—Oic—Arg—OH | $4.1 \times 10^{-9}$ |
| 6 | N,N-dibenzyl-Gly—D—Arg—Arg—Pro—Hyp—Gly—Thia—Ser—D—Tic—Oic—Arg—OH | $2.2 \times 10^{-8}$ |
| 7 | Fmoc—D—Aoc—Arg—Arg—Pro—Hyp—Gly—Thi—Ser—D—Tic—Oic—Arg—OH | $2.2 \times 10^{-8}$ |
| 8 | 2-(4-isobutylphenyl)propionyl-Arg—Arg—Pro—Hyp—Gly—Thi—Ser—D—Tic—Oic—Arg—OH | $2.5 \times 10^{-8}$ |
| 9 | (2-R-(tert.-butylsulfonylmethyl)-3-(1-naphthyl)propionyl-Arg—Arg—Pro—Hyp—Gly—Thi—Ser—D—Tic—Oic—Arg—OH | $1.2 \times 10^{-8}$ |
| 10 | Indole-3-yl-acetyl-Arg—Arg—Pro—Hyp—Gly—Thi—Ser—D—Tic—Oic—Arg—OH | $8.8 \times 10^{-9}$ |
| 11 | 2-(4-isobutylphenyl)propionyl-D—Arg—Arg—Pro—Hyp—Gly—Thi—Ser—D—Tic—Oic—Arg—OH | $1.8 \times 10^{-8}$ |
| 12 | 2-(4-isobutylphenyl)propionyl-6-aminohexanoyl-D—Arg—Arg—Pro—Hyp—Gly—Thi—Ser—D—Tic—Oic—Arg—OH | $7.8 \times 10^{-9}$ |
| 13 | 6-(4-benzoyl-benzoylamino)hexanoyl-D—Arg—Arg—Pro—Hyp—Gly—Thi—Ser—D—Tic—Oic—Arg—OH | $2.7 \times 10^{-8}$ |
| 14 | Fmoc—Aeg(Fmoc)—D—Arg—Arg—Pro—Hyp—Gly—Thi—Ser—D—Tic—Oic—Arg—OH | $1.5 \times 10^{-8}$ |
| 15 | Fmoc—(4-aminocyclohexylcarbonyl)-D—Arg—Arg—Pro—Hyp—Gly—Thi—Ser—D—Tic—Oic—Arg—OH | $2.5 \times 10^{-8}$ |
| 16 | 1,8-naphthalimidoacetyl-D—Arg—Arg— | $7.8 \times 10^{-9}$ |

TABLE 1-continued

| Ex. No. | Sequence | IC$_{50}$ (pulmonary artery) |
|---|---|---|
| 17 | Pro—Hyp—Gly—Thi—Ser—D—Tic—Oic—Arg—OH (2-R-(tert.-butylsulfonylmethyl)-3-(1-naphthyl)-propionyl-D—Arg—Arg—Pro—Hyp—Gly—Thi—Ser—D—Tic—Oic—Arg—OH | $8.3 \times 10^{-9}$ |
| 18 | Indol-3-yl-acetyl-D—Arg—Arg—Pro—Hyp—Gly—Thi—Ser—D—Tic—Oic—Arg—OH | $6.2 \times 10^{-9}$ |
| 19 | Fmoc-(4-aminocyclohexylcarbonyl)-Arg—Pro—Hyp—Gly—Thi—Ser—D—Tic—Oic—Arg—OH | |
| 20 | 7-theophyllineacetyl-Arg—Pro—Hyp—Gly—Thi—Ser—D—Tic—Oic—Arg—OH | |
| 21 | N-benzoyl-D—Arg—Arg—Pro—Hyp—Gly—Thi—Ser—D—Tic—Oic—Arg—OH | |
| 22 | Fmoc—Aeg(Fmoc)—Arg—Pro—Hyp—Gly—Thi—Ser—D—Tic—Oic—Arg—OH | |
| 23 | Fmoc—D—Lys—Arg—Pro—Hyp—Gly—Thi—Ser—D—Tic—Oic—Arg—OH | |
| 24 | Fmoc—Arg—Pro—Hyp—Gly—Thi—Ser—D—Tic—Oic—Arg—OH | |
| 25 | Fmoc—Oic—Arg—Pro—Hyp—Gly—Thi—Ser—D—Tic—Oic—Arg—OH | |
| 26 | Fmoc-trans-4-aminomethylcyclohexylcarbonyl-Arg—Pro—Hyp—Gly—Thi—Ser—D—Tic—Oic—Arg—OH | |

For some selected compounds, the time until the strips of vessel have again reached their maximum sensitivity to $2 \times 10^{-7}$ mol/l bradykinin after replacement of the peptide-containing by a "simple" buffer was also determined in the experimental arrangement described above. This time is called T$_{50}$ and is a measure of the duration of action. The values for this T$_{50}$ found by calculation are listed in Table 2:

TABLE 2

| Ex. No. | Sequence | T$_{50}$ (pulmonary artery) |
|---|---|---|
| 1 | Fmoc—D—Arg—Arg—Pro—Hyp—Gly—Thia—Ser—D—Tic—Oic—Arg—OH | 143.3 min |
| 2 | Fmoc—Aoc—D—Arg—Arg—Pro—Hyp—Gly—Thia—Ser—D—Tic—Oic—Arg—OH | 253.3 min |
| 3 | Dibenzylacetyl-D—Arg—Arg—Pro—Hyp—Gly—Thia—Ser—D—Tic—Oic—Arg—OH | 67.3 min |
| 4 | Cyclohexylcarbonyl-D—Arg—Arg—Pro—Hyp—Gly—Thia—Ser—D—Tic—Oic—Arg—OH | 76.7 min |
| 5 | Fmoc-ε-Aminocaproyl-D—Arg—Arg—Pro—Hyp—Gly—Thia—Ser—D—Tic—Oic—Arg—OH | 314.4 min |

Selected compounds were likewise investigated in vivo in the test described below:

Antiinflammatory effect after systemic administration: carrageenan-induced edema of the rat paw Method The test chosen for the acute systemic antiinflammatory effect is the carrageenan-induced edema of the rat paw by the method described by Winter C. A. et al., Proc. Soc. Exp. Biol. (N.Y.), 111, 544 (1962). Male Sprague-Dawley rats weighing about 170 g in groups of 5 animals receive the substances to be tested subcutaneously dissolved in distilled water (1 ml/kg bodyweight). 15 min later, after measurement of the initial volume of the paw, 0.1 ml of 0.5% strength carrageenan solution is injected under ether anesthesia into the left rear paw. The increase in volume of the swelling is measured 3 and 6 h later, Controls receive only the vehicle. The paw volume is reported in ml (mean and standard deviation). The results are compiled in Table 3.

TABLE 3

| Exp. No. | Dose [mg/kg] | Paw volume before [ml] | Increase in paw volume after 3 h [ml] | after 6 h [ml] |
|---|---|---|---|---|
| Control | | 1.28 ± 0.06 | 0.67 ± 0.16 | 0.42 ± 0.10 |
| 1 | 0.1 | 1.35 ± 0.11 | 0.13 ± 0.06 | 0.14 ± 0.05 |
| | 1.0 | 1.36 ± 0.03 | 0.11 ± 0.05 | 0.08 ± 0.01 |
| Control | | 1.33 ± 0.02 | 0.50 ± 0.10 | 0.44 ± 0.03 |
| 2 | 0.1 | 1.32 ± 0.06 | 0.13 ± 0.04 | 0.29 ± 0.08 |
| | 1.0 | 1.29 ± 0.03 | 0.19 ± 0.06 | 0.27 ± 0.06 |
| Control | | 1.24 ± 0.04 | 0.62 ± 0.11 | 0.54 ± 0.11 |
| 3 | 0.1 | 1.23 ± 0.05 | 0.19 ± 0.07 | 0.22 ± 0.14 |
| Control | | 1.24 ± 0.04 | 0.62 ± 0.11 | 0.54 ± 0.11 |
| 4 | 0.1 | 1.21 ± 0.05 | 0.17 ± 0.08 | 0.31 ± 0.10 |
| Control | | 1.33 ± 0.02 | 0.50 ± 0.10 | 0.44 ± 0.03 |
| 5 | 0.1 | 1.38 ± 0.08 | 0.18 ± 0.04 | 0.20 ± 0.06 |
| | 1.0 | 1.33 ± 0.09 | 0.13 ± 0.03 | 0.17 ± 0.06 |
| Control | | 1.24 ± 0.04 | 0.62 ± 0.11 | 0.54 ± 0.11 |
| 6 | 0.1 | 1.25 ± 0.02 | 0.31 ± 0.06 | 0.40 ± 0.11 |

The therapeutic benefits of the peptides according to the invention embrace all pathological states which are mediated, induced or assisted by bradykinin and peptides related to bradykinin. This includes, inter alia, injuries such as wounds, burns, rashes, erythema, edema, tonsilitis, arthritis, asthma, allergies, rhinitis, shock, inflammations, pancreatitis, low blood pressure, pain, pruritus etc., and changes in sperm motility.

The invention therefore relates to the use of peptides of the formula I as medicines and to pharmaceutical products which contain these compounds.

Pharmaceutical products contain an effective amount of the active substance of the formula I—singly or in combination—together with an inorganic or organic pharmaceutically utilizable excipient.

Administration can take place enterally, parenterally—such as, for example, subcutaneously, i.m. or i.v.—sublingually, epicutaneously, nasally, rectally, intravaginally, intrabuccally or by inhalation. The dosage of the active substance depends on the warm-blooded species, the body weight, age and on the mode of administration.

The pharmaceutical products of the present invention are prepared in dissolving, mixing, granulating and coating processes known per se.

For the form for oral administration or for administration onto the mucous membranes, the active compounds are mixed with the additives customary for this purpose, such as excipients, stabilizers or inert diluents and converted by conventional methods into suitable dosage forms such as tablets, coated tablets, hard gelatin capsules, aqueous, alcoholic or oily suspensions, or aqueous, alcoholic or oily solutions. Examples of inert vehicles which can be used are gum arabic, magnesia, magnesium carbonate, potassium phosphate, lactose, glucose, magnesium stearyl fumarate or starch, especially corn starch. In this connection, preparation can take place both as dry and wet granules. Examples of suitable oily excipients or solvents are vegetable or animal oils, such as sunflower oil and fish liver oil.

A product for topical administration can be in the form of an aqueous or oily solution, lotion, emulsion or jelly, ointment or greasy ointment or, if possible, in the form of a spray, it being possible where appropriate to improve the adhesion by adding a polymer.

For the form for intranasal administration, the compounds are mixed with the additives customary for this purpose, such as stabilizers or inert diluents, and converted by conventional methods into suitable dosage forms such as aqueous, alcholic or oily suspensions or aqueous, alcoholic or oily solutions. It is possible to add to aqueous intranasal preparations chelating agents, ethylenediamine-N,N,N',N'-tetraacetic acid, citric acid, tartaric acid or the salts thereof. Administration of the nasal solutions can take place by means of metering atomizers or as nasal drops with viscosity-increasing content, or nasal gels or nasal creams.

It is possible to use for administration by inhalation atomizers or compressed gas packs using inert carrier gases.

For intravenous, subcutaneous, epicutaneous or intradermal administration, the active compounds or the physiologically tolerated salts thereof are converted, if required with the pharmaceutically customary ancillary substances, for example for rendering isotonic or adjusting the pH, as well as solublizers, emulsifiers or other ancillary substances, into a solution, suspension or emulsion.

Because of the short half-lives of some of the described medicinal substances in body fluids, it is sensible to employ injectable depot preparations. Examples of pharmaceutical forms which can be used are oily crystal suspensions, microcapsules, rods or implants, it being possible for the latter to be composed of tissue-compatible polymers, especially biodegradable polymers such as, for example, based on polylactic acid/polyglycolic acid copolymers or human albumin.

A suitable dose range for forms for topical and inhalation administration are solutions with 0.001–5 mg/kg, and 0.001–10 mg/kg are suitable for systemic administration forms.

List of abbreviations:

The abbreviations used for amino acids correspond to the three-letter code customary in peptide chemistry as is described in Europ. J. Biochem. 138, 9 (1984). Other abbreviations used are listed below.

| Acm | Acetamidomethyl |
|---|---|
| Aeg | N-(2-aminoethyl)glycine |
| ε-Ahx | ε-Aminohexanoyl |
| Aoc | cis, endo-2-azabicyclo[3.3.0]octane-3-S-carbonyl |
| Boc | tert.-Butyloxycarbonyl |
| But | tert.-Butyl |
| Bzl | Benzyl |
| Cbz | Benzyloxycarbonyl |
| CDF | Chloro-(D)-phenylalanyl |
| Cha | Cyclohexylalanyl |
| Chg | Cyclohexylglycyl |
| Cl-Z | 4-Chloro-benzyloxycarbonyl |
| Dic | Dihydroindolecarbonyl |
| DMF | Dimethylformamide |
| DOMT | O-Methyl-(D)-threonyl |
| Dnp | 2,4-Dinitrophenyl |
| Fmoc | 9-Fluorenylmethyloxycarbonyl |
| MDY | O-Methyl-(D)-tyrosyl |
| Me | Methyl |
| 4-Mebzl | 4-Methylbenzyl |
| Mtr | 4-Methoxy-2,3,6-trimethylphenyl-sulfonyl |
| Mts | Mesitylene-2-sulfonyl |
| Nal | 2-Naphthylalanyl |
| NMP | N-Methylpyrrolidine |
| Npg | Neopentylglycyl |
| Oic | cis-endo-Octahydroindole-2-carbonyl |
| Opr | Isoxazolidin-3-ylcarbonyl |
| Pal | Pyridylalanyl |
| Pmc | 2,2,5,7,8-Pentamethylchroman-6-sulfonyl |
| Tbg | tert.-Butylglycyl |
| TBTU | 2-(1H-Benzotriazol-1-yl)-1,1,3,3-tetramethyl-uronium tetrafluoroborate |
| tBu | tert.-Butyl |
| Tcs | 4-Methylphenylsulfonyl |
| TFA | Trifluoroacetic acid |
| Thia | 2-Thienylalanyl |
| Tic | 1,2,3,4-Tetrahydroisoquinolin-3-ylcarbonyl |
| TOTU | O-[(Cyano-(ethoxycarbonyl)methylidene)amino]-1,1,3,3-tetramethyluronium tetrafluoroborate |
| Trt | Trityl |

The following examples are intended to illustrate the preferred methods for the solid-phase synthesis of the peptides according to the invention without meaning to restrict the invention thereto.

The following amino acid derivatives were used, inter alia:

Fmoc-Arg(Mtr)-OH, Fmoc-D-Arg(Mtr)-OH, Fmoc-D-Arg(Pmc)-OH, Boc-(D)-Arg-OH, Fmoc-Arg(Pmc)-OH, Fmoc-Hyp-OH, Fmoc-Pro-OObt, Fmoc-Gly-OObt, Fmoc-Phe-OObt, Fmoc-Ser(tBu)-OObt, Fmoc-(D)-Tic-OH, Fmoc-Gln-OH, Fmoc-Aoc-OH, Fmoc-Thia-OH, Fmoc-Oic-OH, Fmoc-Leu-OH, Fmoc-Lys(Boc)-OH, Fmoc-ε-Ahx-OH.

Example 1:

Fmoc-D-Arg-Arg-Pro-Hyp-Gly-Thia-Ser-D-Tic-Oic-Arg-OH was assembled stepwise using the Fmoc method on a p-benzyloxybenzyl alcohol-resin from Novabiochem (loading about 0.5mmol/g of resin) esterified with Fmoc-Arg(Mtr)-OH using a model 430 A peptide synthesizer from Applied Biosystems. 1 g of the resin was employed, and the synthesis was carried out using a synthesis program modified for the Fmoc method.

In each case 1 mmol of the amino acid derivatives with free carboxyl group was weighed together with 0.95 mmol of HOObt into the cartridges of the synthesizer. The preactivation of these amino acids took place directly in the cartridges by dissolving in 4 ml of DMF and adding 2 ml of a 0.55 mol/l solution of diisopropylcarbodiimide in DMF. The HOObt esters of the other amino acids were dissolved in 6 ml of NMP and then coupled just like the amino acids which have been preactivated in situ onto the resin which had previously been deblocked with 20% piperidine in DMF. The last amino acid derivative coupled on was Fmoc-D-Arg(Pmc)-OH, which was not subsequently deprotected with piperidine. After the synthesis was complete, the peptide was cleaved off the resin with simultaneous removal of the side-chain protective groups with trifluoroacetic acid using thioanisole and ethanedithiol as cation traps. The residue obtained after the trifluoroacetic acid had been stripped off was digested with ethyl acetate, and centrifuged, several times. The remaining residue was chromatographed on ®Sephadex LH 20 with 10% strength acetic acid. The fractions containing the pure peptide were combined and freeze-dried.

MS(FAB): 1526.9

Example 2:
Fmoc-Aoc-D-Arg-Arg-Pro-Hyp-Gly-Thia-Ser-D-Tic-Oic-Arg-OH

The title compound was obtained by initially eliminating the N-terminal Fmoc protective group using piperidine/dimethylformamide from a peptide-resin with the sequence Fmoc-D-Arg(Pmc)-Arg(Mtr)-Pro-Hyp-Gly-Thia-Ser(But)-D-Tic-Oic-Arg(Mtr)-resin which had previously been obtained in analogy to Example 1, washing the resin with DMF and then coupling on Fmoc-Aoc-OH using the uronium coupling reagent TOTU. The peptide was then cleaved off the resin with a mixture of trifluoroacetic acid, trimethylsilyl bromide and m-cresol. Purification took place in analogy to the process described in Example 1.

MS(FAB): 1663.8

The following examples were prepared in analogy to Example 2

Example 3: Dibenzylacetyl -D-Arg-Arg-Pro-Hyp-Gly-Thia-Ser-D-Tic-Oic-Arg-OH MS(FAB): 1526.7

Example 4: Cyclohexylcarbonyl-D-Arg-Arg-Pro-Hyp-Gly-Thia-Ser-D-Tic-Oic-Arg-OH MS(FAB): 1414.7

Example 5: Fmoc-ε-aminohexanoyl-D-Arg-Arg-Pro-Hyp-Gly-Thia-Ser-D-Tic-Oic-Arg-OH MS(FAB): 1639.6

Example 6: N, N-Dibenzyl-glycyl-D-Arg-Arg-Pro-Hyp-Gly-Thia-Ser-D-Tic-Oic-Arg-OH MS(FAB): 1542.2

Example 7: Fmoc-D-Aoc-Arg -Arg-Pro-Hyp-Gly-Thi-Ser-D-Tic-Oic-Arg-OH MS(FAB): 1663.8

Example 8: 2-(4-Isobutylphenyl)-propionyl-Arg-Arg-Pro-Hyp-Gly-Thi-Ser-D-Tic-Oic-Arg-OH MS(FAB): 1493

Example 9: (2-R-(tert.-butylsulfonylmethyl)-3-(1-naphthyl)propionyl-Arg-Arg-Pro-Hyp-Gly-Thi-Ser-D-Tic-Oic-Arg-OH MS(FAB): 1621

Example 10: Indol-3-yl-acetyl-Arg-Arg-Pro-Hyp-Gly-Thi-Ser-D-Tic-Oic-Arg-OH MS(FAB): 1462

Example 11: 2-(4-Isobutylphenyl)propionyl-D-Arg-Arg-Pro-Hyp-Gly-Thi-Ser-D-Tic-Oic-Arg-OH MS(FAB): 1493

Example 12: 2-(4-Isobutylphenyl)propionyl-6-aminohexanoyl-D-Arg-Arg-Pro-Hyp-Gly-Thi-Ser-D-Tic-Oic-Arg-OH MS(FAB): 1606

Example 13: 6-(4-Benzoyl-benzoylamino)hexanoyl-D-Arg-Arg-Pro-Hyp-Gly-Thi-Ser-D-Tic-Oic-Arg-OH MS(FAB): 1625.8

Example 14: Fmoc-Aeg(Fmoc)-D-Arg-Arg-Pro-Hyp-Gly-Thi-Ser-D-Tic-Oic-Arg-OH MS(FAB): 1849.8

Example 15: Fmoc-(4-aminocyclohexylcarbonyl)-D-Arg-Arg-Pro-Hyp-Gly-Thi-Ser-D-Tic-Oic-Arg-OH MS(FAB): 1652

Example 16: 1,8 -Naphthal imidoacetyl -D-Arg-Arg-Pro-Hyp-Gly-Thi-Ser-D-Tic-Oic-Arg-OH MS(FAB): 1542.3

Example 17: (2-R-(tert.-butylsulfonylmethyl)-3-(1-naphthyl)propionyl-D-Arg-Arg-Pro-Hyp-Gly-Thi-Ser-D-Tic-Oic-Arg-OH MS(FAB): 1621.9

Example 18: Indol-3-yl-acetyl-D-Arg-Arg-Pro-Hyp-Gly-Thi-Ser-D-Tic-Oic-Arg-OH MS(FAB): 1462

Example 19: Fmoc-(4-aminocyclohexylcarbonyl)-Arg-Pro-Hyp-Gly-Thi-Ser-D-Tic-Oic-Arg-OH MS(FAB): 1496

Example 20: 7-Theophyllineacetyl-Arg-Pro-Hyp-Gly-Thi-Ser-D-Tic-Oic-Arg-OH MS(FAB): 1369

Example 21: N-Benzoyl -D-Arg-Arg-Pro-Hyp-Gly-Thi-Ser-D-Tic-Oic-Arg-OH MS(FAB): 1410

Example 22: Fmoc-Aeg(Fmoc)-Arg-Pro-Hyp-Gly-Thi-Ser-D-Tic-Oic-Arg-OH MS(FAB): 1694

Example 23: Fmoc-D-Lys-Arg-Pro-Hyp-Gly-Thi-Ser-D-Tic-Oic-Arg-OH MS(FAB): 1500

Example 24: Fmoc-Arg-Pro-Hyp-Gly-Thi-Ser-D-Tic-Oic-Arg-OH MS(FAB): 1371

Example 25: Fmoc-Oic-Arg-Pro-Hyp-Gly-Thi-Ser-D-Tic-Oic-Arg-OH MS(FAB): 1523

Example 26: Fmoc-trans-4 -aminomethylcyclohexyl-carbonyl-Arg-Pro-Hyp-Gly-Thi-Ser-D-Tic-Oic-Arg-OH MS(FAB): 1511

We claim:

1. A peptide of the formula I $$Z\text{-}P\text{-}A\text{-}B\text{-}C\text{-}E\text{-}F\text{-}K\text{-}(D)Q\text{-}G\text{-}M\text{-}F'\text{-}I \qquad (i)$$

in which

Z is Fmoc, dibenzylacetyl, cyclohexylcarbonyl, N,N-dibenzyl-glycyl, 2-(4-isobutylphenyl)propionyl, (2-R-(tert butylsulfonylmethyl)-3-(1-naphthyl)propionyl, indole-3-yl-acetyl, 6-(4-benzoyl-benzoylamino)hexanoyl, 1,8-naphthalimidoacetyl, 7-theophyllineacetyl or N-benzoyl;

P is a direct linkage, Aoc, ε-aminohexanoyl, D-Aoc, Aeg(Fmoc), 4-aminocyclohexylcarbonyl or Oic;

A is (D)- or (L)-Arg, (D)- or (L)-Lys, or is a bond;

B is Arg;

C is Pro-Hyp-Gly;

E is Thia;

F is Ser;

K is a direct linkage;

Q is Tic;

M is a direct linkage;

G is cis-endo-, cis-exo-, trans-octahydroindole-2-carboxylic acid;

F' is Arg; and

I is OH.

2. A method for the treatment of inflammation in a mammal wherein the inflammation is mediated, induced or assisted by bradykinin or peptides related to bradykinin, which comprises administering to said mammal an anti-inflammatorily effective amount of a peptide of the formula I as claimed in claim 1.

3. A pharmaceutical composition containing a peptide of the formula I as claimed in claim 1.

* * * * *